(12) United States Patent
Aguilar et al.

(10) Patent No.: US 8,244,475 B2
(45) Date of Patent: Aug. 14, 2012

(54) COUPLING HUMAN NEURAL RESPONSE WITH COMPUTER PATTERN ANALYSIS FOR SINGLE-EVENT DETECTION OF SIGNIFICANT BRAIN RESPONSES FOR TASK-RELEVANT STIMULI

(75) Inventors: Mario Aguilar, Cary, NC (US); Ming Qian, Raleigh, NC (US)

(73) Assignee: Teledyne Scientific & Imaging, LLC, Thousand Oaks, CA (US)

( * ) Notice: Subject to any disclaimer, the term of this patent is extended or adjusted under 35 U.S.C. 154(b) by 1264 days.

(21) Appl. No.: 11/965,325

(22) Filed: Dec. 27, 2007

(65) Prior Publication Data

US 2012/0172743 A1  Jul. 5, 2012

(51) Int. Cl.
*G01N 33/48* (2006.01)
*G06F 7/60* (2006.01)
*G06G 7/58* (2006.01)

(52) U.S. Cl. ............ 702/19; 600/544; 600/545; 702/20; 703/2; 703/11

(58) Field of Classification Search .................. None
See application file for complete search history.

(56) References Cited

U.S. PATENT DOCUMENTS

| | | | |
|---|---|---|---|
| 4,753,246 A | 6/1988 | Freeman | |
| 5,617,872 A | 4/1997 | Scinto | |
| 5,632,282 A | 5/1997 | Hay | |
| 5,649,061 A | 7/1997 | Smyth | |
| 5,797,853 A | 8/1998 | Musha | |
| 5,846,208 A | 12/1998 | Pichlmayr | |
| 6,090,051 A | 7/2000 | Marshall | |
| 6,092,058 A | 7/2000 | Smyth | |
| 6,102,870 A | 8/2000 | Edwards | |
| 6,230,049 B1 | 5/2001 | Fischell | |
| 6,434,419 B1 | 8/2002 | Gevins | |
| 6,572,562 B2 | 6/2003 | Marshall | |
| 6,931,274 B2 | 8/2005 | Williams | |
| 7,147,327 B2 | 12/2006 | Stark et al. | |
| 7,231,245 B2 | 6/2007 | Greenwald | |
| 7,344,251 B2 | 3/2008 | Marshall | |
| 7,438,418 B2 | 10/2008 | Marshall | |
| 2002/0099305 A1 | 7/2002 | Fukushima | |
| 2007/0185697 A1 | 8/2007 | Tan | |
| 2007/0236488 A1 | 10/2007 | Mathan | |
| 2008/0188777 A1 | 8/2008 | Bedziouk | |

OTHER PUBLICATIONS

Adam D. Gerson, Cortically Coupled Computer Vision for Rapid Image Search, IEEE Trans on Neural Systems and Rehabilitation Engineering, vol. 14. No. 2, pp. 174-179 Jun. 2006.
Lucas C. Parra, Recipes for the linear analysis of EEG, NeuroImage 28 (2005) pp. 326-341.
Simon Thorpe, Speed of Processing in the human visual system, Nature, vol. 381, Jun. 6, 1996, pp. 520-522.
Lawrence M. Ward, Synchronous neural oscillations and cognitive processes, Trends in Cognitive Science vol. 7 No. 12 Dec. 2003, pp. 553-559.
Canan Basar-Eroglu, P300-response: possible psychophysiological correlates in delta and theta frequency channels, A review, International Journal of Psychophysiology 13 (1992).
W. Klimesch, Induced alpha band power changes in the human EEG and attention, Neuroscience Letters 244 (1998) 73-76.
Eric Granholm, Pupillometric measures of cognitive and emotional processes, International Journal of Psychophysiology 52 (2004) 1-6.

*Primary Examiner* — Shubo Zhou
(74) *Attorney, Agent, or Firm* — Eric A. Gifford

(57) ABSTRACT

The human neural response is coupled with computer pattern analysis for robust single-event detection of significant non-stationary brain responses triggered upon occurrence of a task-relevant stimulus. Classifier performance is enhanced fusing together the outputs of multiple different classifiers albeit multiple spatial classifiers to extract a temporal pattern as the brain response evolves, time and frequency-based spatio-temporal classifiers, and/or EEG and pupillary classifiers.

20 Claims, 13 Drawing Sheets

COUPLING HUMAN NEURAL RESPONSE WITH COMPUTER PATTERN ANALYSIS FOR SINGLE-EVENT DETECTION OF SIGNIFICANT BRAIN RESPONSES FOR TASK-RELEVANT STIMULI

GOVERNMENT LICENSE RIGHTS

The U.S. Government has a paid-up license in this invention and the right in limited circumstances to require the patent owner to license others on reasonable terms as provided for by the terms of (contract No. HM1592-05-C-0041) awarded by DARPA-DSO.

BACKGROUND OF THE INVENTION

1. Field of the Invention

This invention relates to the use of EEG recordings to detect brain responses for task-relevant stimuli.

2. Description of the Related Art

Electroencephalography (EEG) is the neurophysiologic measurement of the electrical activity 10 of the brain recording from electrodes 12 placed on the scalp as depicted in FIG. 1. The EEG signals contain data and patterns of data associated with brain activity. Cognitive neuroscience techniques use a multi-channel spatial classifier 14 to analyze the EEG signals to infer the existence of certain brain states 16. These techniques are used to study the brain and to perform clinical diagnosis. These techniques may also be used to detect significant brain responses to task-relevant stimuli.

The detection of such a response may be fed back or used in some manner in conjunction with the task. For example, the brain response could be used in a classification system to detect and classify visual, auditory or information stimuli, a warning system to detect potential threats, a lie detector system etc. The detection of a significant brain response does not classify the stimulus but raises an alert that the user's brain has responded in a significant way. Some of the alerts will be false positives or 'false alarms' but if the system is configured properly to reduce the false alarm rate the detected brain responses may be very useful. Current systems try to improve the signal-to-noise ratio (SNR) of the EEG signals to reduce the false alarm rate at a given detection probability.

EEG signals represent the aggregate activity of millions of neurons on the cortex and have high time-resolution (capable of detecting changes in electrical activity in the brain on a millisecond-level). Evidence suggests significant amplitude differences between trial-averaged EEG responses triggered by task-relevant stimuli versus trial-averaged EEG responses triggered by neutral stimuli. The benefit of integrating EEG responses across multiple trials is to suppress the task-unrelated background EEG and project out the task-relevant EEG saliently, i.e. improve the signal-to-noise ratio.

One example of a trial-averaged system is described by Tan in US Pub No. 2007/0185697 entitled "Using Electroencephalograph Signals for Task Classification and Activity Recognition". To train the classifier, Tan collects labeled EEG data while a person is performing a task and divides the data into overlapping time windows e.g. 2 second windows with a 50% overlap over a 12 second interval. The time dimension is then removed from each of the time windows. Features are extracted from each dimensionless window, aggregated and then pruned to form a feature set for a single classifier. The trained classifier is used to classify brain states in unlabeled EEG by dividing the data into overlapping time windows and then processing each window to remove the time dimension. The 'pruned' features are extracted for each window and presented to the same classifier. The results are then averaged over time to improve SNR.

In other contexts, the event or task stimulus cannot be trial-averaged. For example, the stimulus may occur only once ("single-event"). Alternately, the application may need to classify the brain response in real-time. In Tan, the user repeats the task for several seconds alloying the classifier to process multiple 2-3 second windows before classifying the task. As Tan's method is directed at evaluating the effectiveness of a computer-user interface, the stimulus can be repeated and a delayed classification is acceptable.

The biggest challenge of single-event real-time detection is to overcome the low SNR problem imposed by event-unrelated background EEG responses that usually have larger amplitude than event-related responses and could completely obscure the later. Recent advances in adaptive signal processing have demonstrated significant single trial detection capability by integrating EEG data spatially across multiple channels of high density EEG sensors (L. Parra et al, "Single trial Detection in EEG and MEG: Keeping it Linear", Neurocomputing, vol. 52-54, June 2003, pp. 177-183, 2003 and L. Parra et al, "Recipes for the Linear Analysis of EEG", NeuroImage, 28 (2005), pp. 242-353)). The linear (LDA) classifier provides a weighted sum of all electrodes over a predefined temporal window as a new composite signal that serves as a discriminating component between responses to target versus distractor stimuli.

A rapid serial visual presentation (RSVP) system for triaging imagery is an example of a single-event system in which cognitive neuroscience techniques for classifying brain states have been employed (A. D. Gerson et al "Cortical-coupled Computer Vision for Rapid Image Search", IEEE Transaction on Neural Systems and Rehabilitation Engineering, June 2006). The US military and intelligence agencies generate enormous amounts of imagery that require visual examination to identify possible targets of interest for further inspection. In the RSVP system, electrodes are placed on an analyst's scalp, image clips are displayed to the analyst at a rate of approximately 10 per second and a multi-channel LDA classifier is employed to classify the brain response to the presentation of each image. If a significant response is indicated, the system flags the image clip for closer inspection.

For both the trial averaged approach and the spatially integrated single trial approach, testing revealed that the event-related EEG response triggered by target detection is most prominent at a certain critical time period after stimulus onset. Thorpe et al "Speed of processing in the human visual system", Nature Vol. 381, pp. 530-532, 6 Jun. 1996 found that the trial averaged ERP generated on target versus distractor trials diverge sharply at 150-200 milliseconds after stimulus onset for a go/no-go image categorization. Para et al applied the LOA classifier in the RSVP on EEG data in a predefined temporal window centering around the time where the target trial averaged ERP most sharply diverged from the distractor trial averaged ERP. Similarly, Gerson used a training window between 400-500 ms following stimulus onset to extract training data. Gerson also recommended using multiple classifiers with different training window onsets to boost triage performance. The training window onsets ranged from 0 to 900 ms in steps of 50 ms with window durations of 50 ms. Once these classifiers were trained, the optimal weight of these classifier outputs was found using logistic regression to discriminate between target and non-target images.

SUMMARY OF THE INVENTION

The present invention provides a method and apparatus of coupling human neural response with computer pattern analysis for robust single-event detection of significant non-stationary brain responses triggered upon occurrence of a task-relevant stimulus.

This is accomplished by measuring EEG data of the user's brain activity from electrodes placed on the user's scalp, subdividing the EEG data into a plurality of different time windows each ranging from 20 ms to 200 ms and more typically 50-100 ms in duration and overlapping, and extracting EEG features from each time window. The extracted features may be time-domain, frequency-domain or a combination thereof.

The extracted features are presented to a respective plurality of computer-implemented spatial classifiers independently trained to detect spatial patterns of the extracted features during different time windows from the occurrence of the task-relevant stimulus and to generate first level outputs indicative of the occurrence or absence of a significant brain response. If the timing of the occurrence of a possible task-relevant stimulus is known, a global window of data ("epoch") can be captured for each stimulus and subdivided into the different local time windows synchronized to that stimulus. If the timing is unknown, a sliding window, suitably overlapping, is used to segment the EEG data and present the extracted features to each spatial classifier. Either the extracted features input to the classifiers or the outputs generated by the classifiers must be delayed in order to time-align the first level outputs. In both cases, the number of classifiers is preferably selected to correspond to the index of a threshold local time window beyond which the final classification performance does not improve. This threshold is typically determined for each human subject due to inter-subject variability in brain response phenomenology but may be based on group statistics.

The plurality of spatial classifier first level outputs are then combined to detect temporal patterns across the different time windows relating to the evolution of the non-stationary brain response to a task-relevant stimulus and to generate a second level output indicative of the occurrence or absence of the significant non-stationary brain response. This combination is suitably performed using either a 'feature-level' or 'decision-level' classifier.

Instead of presenting the time and frequency domain features for each window to the same set of classifiers, they may be presented to different sets of spatial classifiers and their outputs fused to form different second level outputs, one for time-domain features and one for frequency-domain features, which are then fused to form a third level output. Performance may also be enhanced by fusing the EEG results with another classifier that detects the same brain response based on a user's pupillary response. Decision-level fusion of the complementary time and frequency or EEG and pupil modalities is particularly effective. Fusion of the temporal responses, time and frequency domain responses and/or EEG and pupillary responses greatly reduces the false alarm rate for a given detection probability.

In an alternate embodiment, the time and frequency domain features or EEG and pupil classifiers may be implemented using the conventional single-window approach. Furthermore, the pupil classifier may be used by itself to detect significant brain responses. The spatio-temporal architecture improves overall performance but is not required to realize the performance benefits attributable to time/frequency fusion or EEG/pupil fusion.

These and other features and advantages of the invention will be apparent to those skilled in the art from the following detailed description of preferred embodiments, taken together with the accompanying drawings, in which:

DETAILED DESCRIPTION OF THE INVENTION

The present invention provides a method and apparatus of coupling human neural response with computer pattern analysis for enhanced real-time single-event detection of significant non-stationary brain responses triggered upon occurrence of a task-relevant stimulus.

Figure 1:
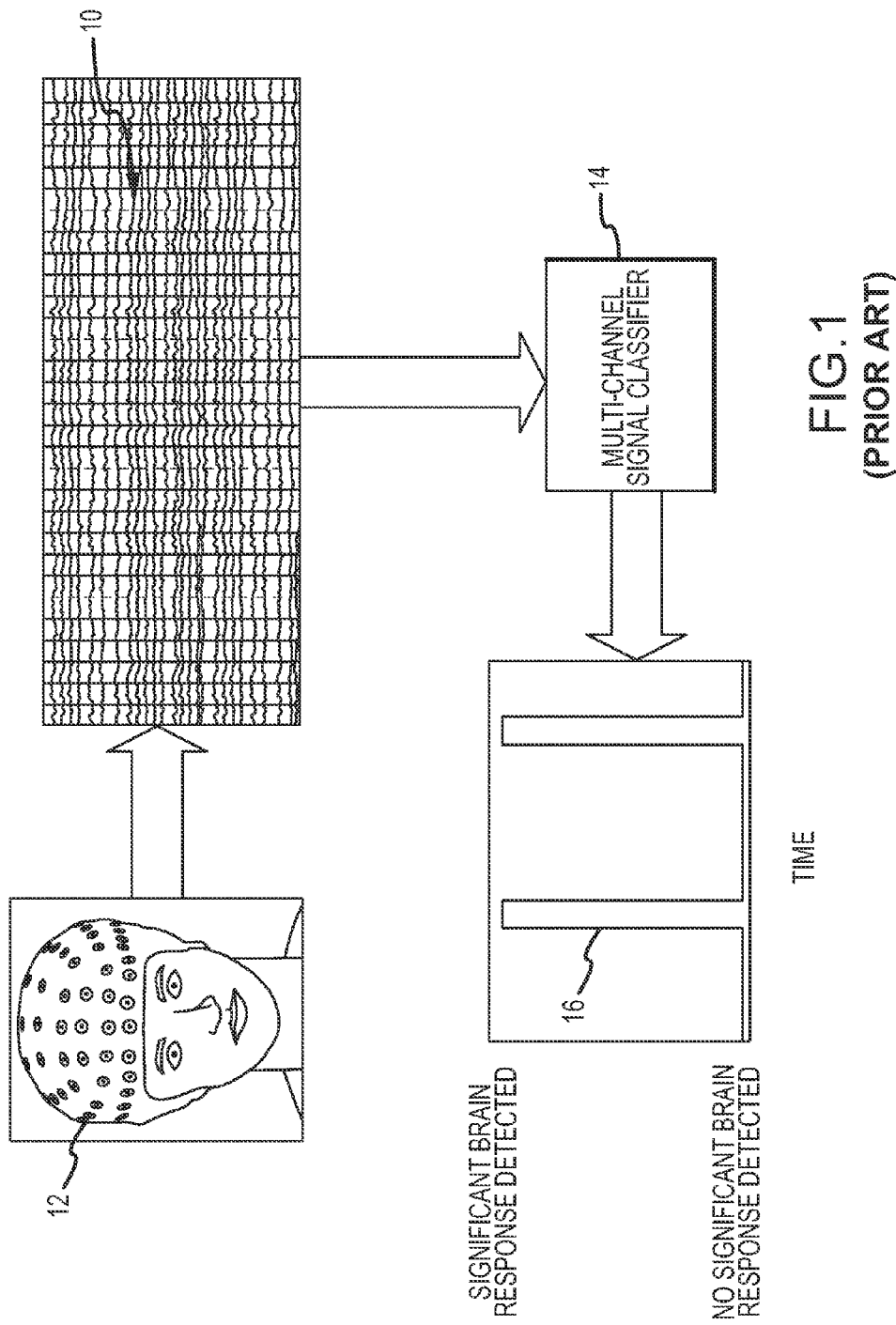
FIG. 1, as described above, is a diagram illustrating the use of a multi-channel spatial classifier to detect significant brain responses from EEG data.
Figure 2:
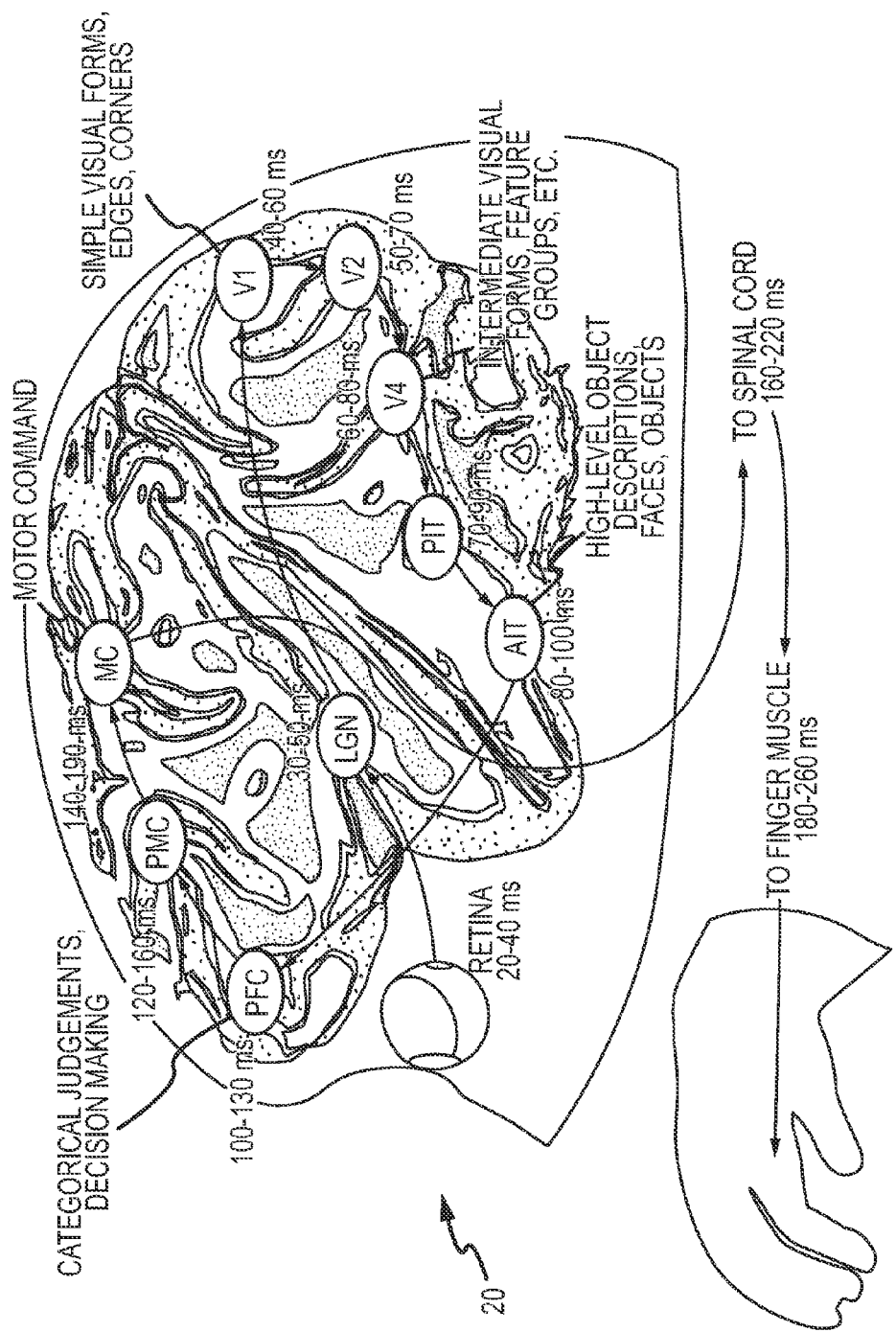
FIG. 2 is a diagram of a primate's brain illustrating the non-stationary brain response in response to a stimulus.

The brain response to stimuli is not a stationary pulse. The brain response reflects neurophysiological activities located in selectively distributed sites of the brain evolving with a continuous time course. FIG. 2 illustrates the evolving brain response 20 in a primate, which would be similar to a human. The precise timing will vary between human and primate and from human subject to human subject. In human subjects, the first indication of brain response to a stimuli occur approximately 80 ms after the onset of the stimuli and may continue for up to approximately 900 ms -1.5 sec as the signal propagates through different areas of the brain.

The brain response to "task-relevant" information is a non-stationary signal distributed across multiple areas of the brain. Specifically, perceptual information from the senses is first processed in primary sensory cortex from where it travels to multiple cortical mid-section areas associated with separately processing the spatial ("Where") and semantic ("What") meaning of the information. The resulting information patterns are matched against expectations, relevance or mismatch at which point signals are relayed to more frontal regions were higher-level decisions can be made about the relevance of the information. If enough evidence exists, a commitment to respond is then made. This suggests that the decision process involves multiple sites (space) across a relative long time window (and time). Our approach to analyzing the EEG signal attempts to capture this spatio-temporal pattern by collecting evidence of this non-stationary signal and combining it to improve detection confidence.

Spatio-Temporal Classifier

Figure 3:
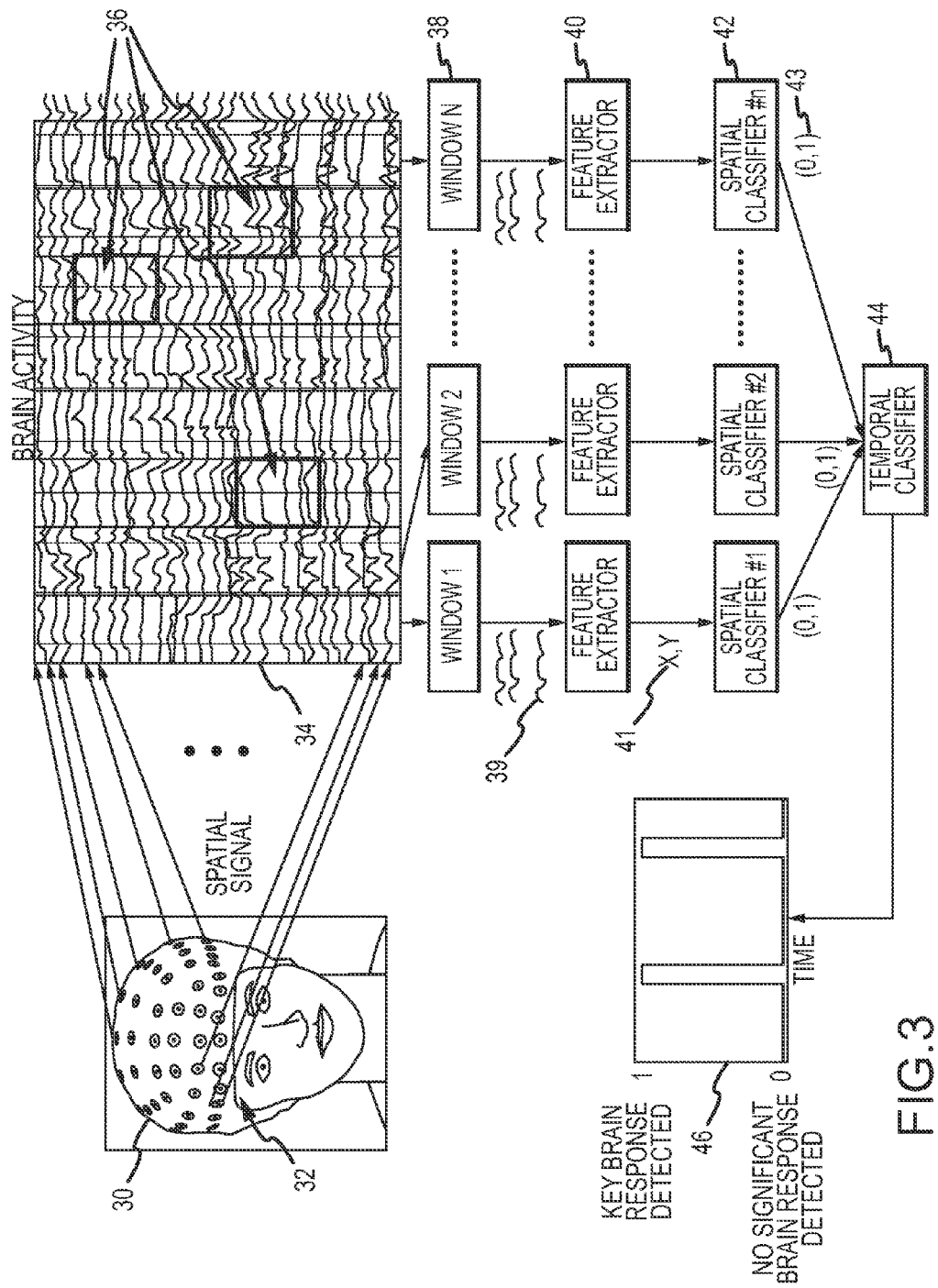
FIG. 3 is a diagram illustrating the use of a multi-channel spatio-temporal classifier to detect significant brain responses from EEG data in accordance with the present invention.

Electrodes 30 on a subject's scalp 32 generate multiple spatial channels of EEG data 34 in response to various stimuli as shown in FIG. 3. Each spatial channel includes a temporal signal 36 typically representative of an amplitude difference between a pair of electrodes. Unlike other methods of detecting brain responses such as MRI, EEG data has a very fine time resolution. To detect significant brain responses to task-relevant stimuli, we configure the classifier to capture the evolving spatio-temporal pattern as the response to the stimuli propagates through certain distributed areas of the brain. In general, the classifier is not classifying the stimulus itself but is deciding whether a significant brain-response has occurred. The classifier may be trained to detect any significant brain response or it may be trained to detect significant brain responses for certain types of task-relevant stimulus e.g. certain targets of interest in images.

Figure 4A:
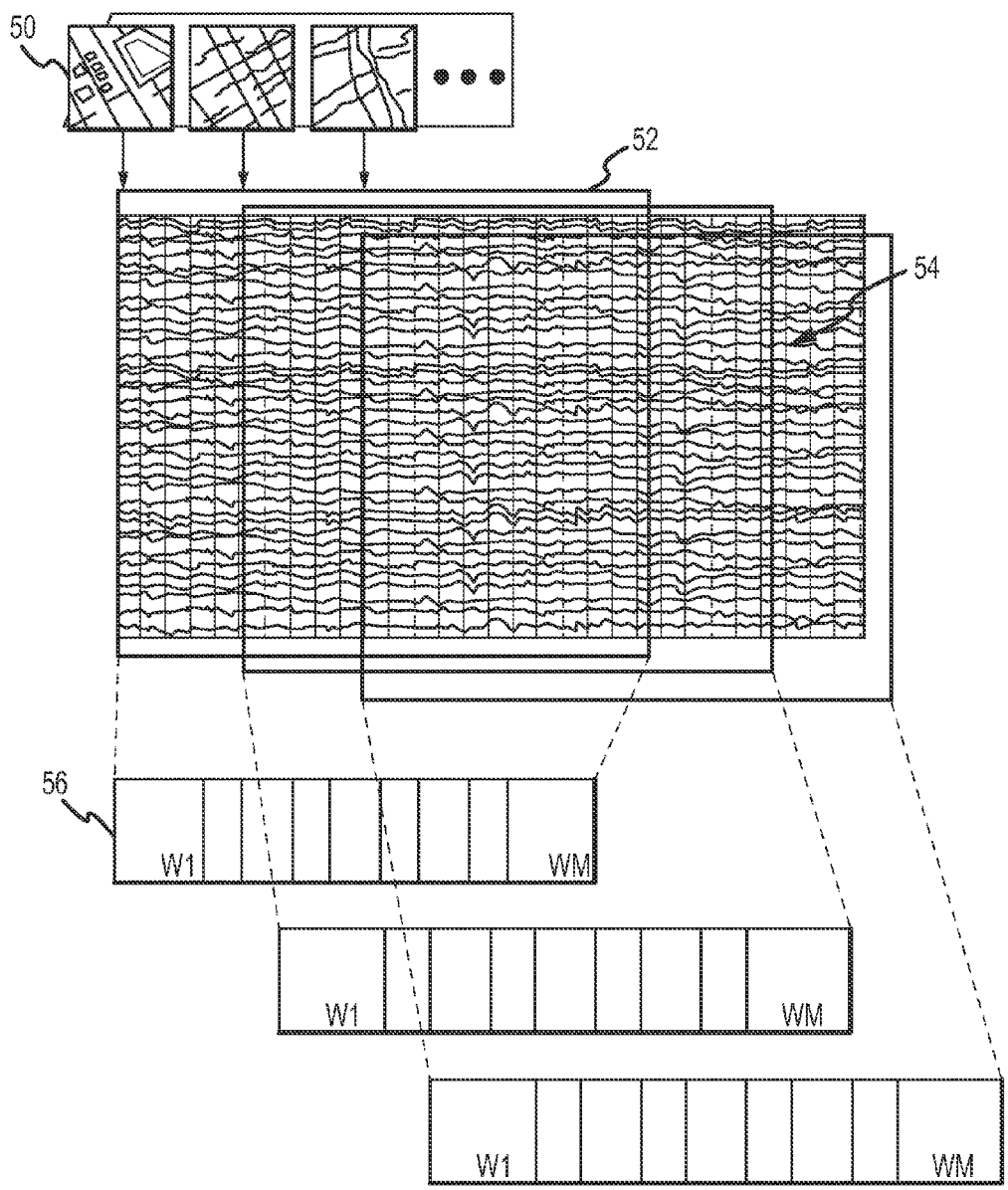
FIGS. 4a and 4b are diagrams illustrating the windowing and presentation of EEG data to the classifiers for discrete and continuous detection systems, respectfully.
Figure 4B:
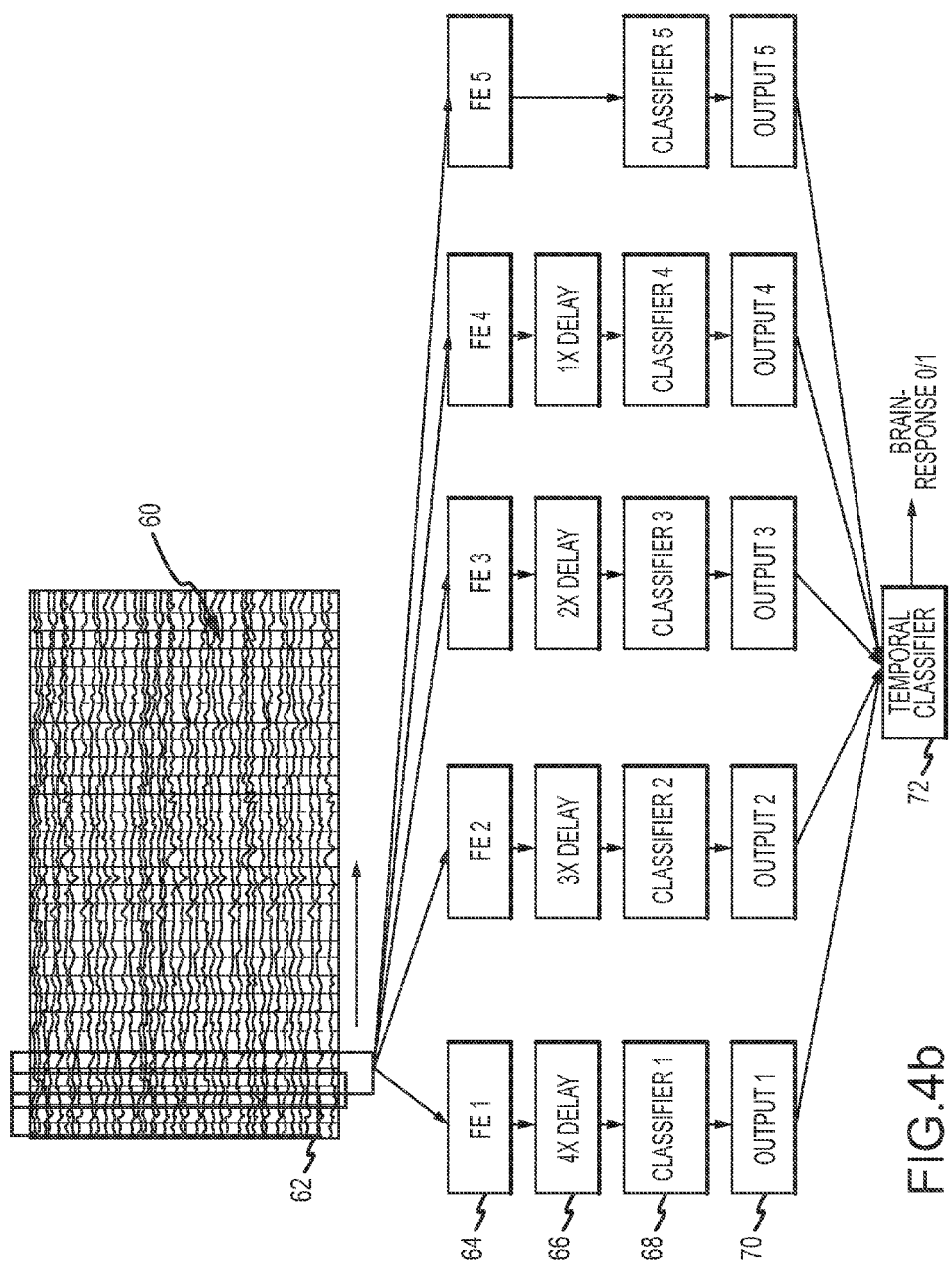

The EEG data is subdivided into a plurality of windows 38 sufficient to capture the temporal evolution of the brain response to a stimulus. Each window contains a different temporal segment of data 39 from the onset of a stimulus for a subset, typically all, of the spatial channels. As will be discussed with reference to FIGS. 4a and 4b, how the data is windowed and presented to the classifier differs if the system presents stimuli at known discrete times such as an RSVP system or if the system continuously senses for the occurrence of stimuli at unknown times.

In order to detect temporal patterns across the different time windows it is useful to control four separate parameters; the window duration, the number of windows, the total temporal window captured and the overlap between windows. The window duration and overlap are typically uniform but could be tailored based on specific training for certain applications. Window duration may be in the range of 20-200 ms and more typically 50-100 ms; long enough to capture signal content with sufficient SNR yet short enough to represent a distinct portion of the non-stationary signal. The number of windows must be sufficient to provide a robust temporal pattern. The total temporal window typically spans the onset of the stimuli to a threshold window beyond which the additional data does not improve results. The threshold may be assigned based on the response of each subject or based on group statistics. The threshold window for most subjects for our experimental stimuli is near 500 ms. Window overlap is typically 25-50%, sufficient to center critical brain response transitions within windows and to provide some degree of temporal correlation between spatial classifiers. Larger overlaps may induce too much correlation and become computationally burdensome.

Feature extractors 40 extract features X, Y, . . . 41 from the respective windows of EEG data. These features may be time-domain features such as amplitude of frequency-domain features such as power or combinations thereof. The extracted features may or may not be the same for each window. To optimize performance and/or reduce the computational load, the nature and number of features will be determined during classifier training, typically for a particular task-relevant application. For example, classifier training may reveal that certain features are better discriminators in early versus late windows. Furthermore, since the temporal evolution of the signal roughly corresponds to its propagation through different areas of the brain features may be extracted from different subsets of spatial channels for the different windows. Training would identify the most important spatial channels for each window.

Once extracted, the features from the different temporal windows are presented to respective spatial classifiers 42. Each classifier is trained based on the extracted features for its particular window to detect a significant brain response for a task-relevant stimulus. The classifier may be trained to recognize any significant brain response or, more typically, it may be trained for a particular task such as image target recognition, word recognition, lie detector, etc. Brain activity is measured and recorded during periods of task relevant and irrelevant stimulation and the classifiers are trained to discriminate between the two states. Specific techniques for training different classifiers are well known in the art. A linear discrimination analysis (LDA) classifier of the type used in single-window RSVP systems was configured and trained for each of the N spatial classifiers. The LDA classifier described by Parra linearly combines the multiple spatial EEG channels to form an aggregate representation of the data. Other linear and non-linear classifiers such as support vector machines (SVM), neural networks or AdaBoost could also be employed. Different classifiers may be used for the different windows. Each classifier 42 generates a first level output 43. The classifiers may be configured to generate either a likelihood output e.g. a continuous value from 0 to 1, or a decision output e.g. a binary value of 0 or 1 depending on the type of fusion used to combine the outputs.

The spatial classifiers' first level outputs are presented to a temporal classifier 44 that combines them to detect temporal patterns across the different time windows relating to the evolution of the non-stationary brain response to task-relevant stimulus and to generate a second level output 46 indicative of the occurrence or absence of the significant non-stationary brain response. In this configuration, the second level output is a binary decision as to the brain state for a current stimulus. Although there is some latency due to data collection e.g. 500 ms from the onset of the stimulus, the processing time is small, approximately 5 ms, so that the system can generate decision level outputs in real-time that keep up with the presentation or occurrence of stimuli.

Feature-level fusion detects the temporal pattern using a global classifier such as a LDA or a relevance vector machine (RVM). The continuous valued outputs of the spatial classifiers are considered as inputs features. For the LDA classifier, let y be the observed vector of spatial classifier output, a weight vector W can be derived based on training data to generate a one-dimension projection $z=W^Ty$ where the dimension of the weight vector W is the number of spatial classifiers M. The projection z serves as an estimate of global pattern. The likelihood that a measurement belongs to the target class is assumed to follow a logistic distribution e.g. $p(H_1|y)=1/(1+e^{-z})$. Receiver operating characteristic (ROC) curves can be obtained by comparing $p(H_1|y)$ to a threshold $\eta$ having a value in [0,1]. The decision rule can be $p(H_1|y) \geq \eta$, out=1 and $p(H_1|y) \leq \eta$, out=0 or vice versa where out=1 represent a classifier's decision to declare detection of significant brain response and out=0 represents a classifier's decision to declare a non-significant brain response. When real data is presented to the temporal classifier, the weight vector W will combine the outputs to discriminate patterns that indicate significant brain response from those that do not.

A RVM classifier models the likelihood that a measurement belongs to the target class as a sigmoid logistic function distribution $p(H_1|y)=1/(1+e^{-f_{RVM}(y)})$ where $f_{RVM}(y)=\Sigma(\alpha_i K(y,y_i)+b)$ for i=1 to M where $K(y,y_i)$ is the kernel function, $\alpha_i$ is the weight parameter for each spatial classifier output and b is a threshold. To determine the $\alpha_i$ using a Bayesian approach, they are encoded to have a sparse prior: statistically independent from each other and follow a zero-mean, Gaussian distribution with variance $\lambda_i^{-1}$; in addition, a gamma distribution is assumed on the hyper-parameter $\lambda_i$. Therefore, prior $\alpha_i$ are highly concentrated around 0 and generate very few nonzero terms in $f_{RVM}(y)$. A maximum a posterior (MAP) estimate for the weight parameters $\alpha_i$ can be obtained by maximizing the posterior distribution of the class labels given the training set. The same decision rule can be applied.

Decision-level fusion detects temporal patterns by optimizing complementarities of the spatial classifiers' binary decisions. Decision-level fusion is implemented to achieve an optimal combination of maximum likelihood estimates achievable between two or more alternative and complementary decisions. Training provides the operating points for the decision-level classifier.

An effective approach is to use Bayesian inference where spatial classifiers' binary decisions are treated as multiple hypotheses that need to be combined optimally. The hypotheses are $H_0$ (distractor) and $H_1$ (task-relevant stimulus). The spatial classifier output vector has joint probability density function $P(y^1, \ldots, y_k|H_j)$ under hypothesis $H_j$, for j=0,1 and k=2, ..., M. For individual local amplitude-based classifiers, they receive as inputs the N-dimension observation vector x (amplitude) and make the decisions based on the LDA classifier outputs (given a fixed value of decision threshold). The decisions drawn from M individual spatial classifiers are denoted as $u_k$, where k=1,2, ..., M and $u_k$=0 if the spatial classifier k decides $H_0$ and $u_k$=1 if the spatial classifier k decides $H_1$. Individual classifier's decision $u_k$ depends only on the spatial classifiers' output vectors y.

$$u_k = \alpha(x_k) = \begin{cases} 0, & \text{spatial classifier } k \text{ decides } H_0 \\ 1, & \text{spatial classifier } k \text{ decides } H_1 \end{cases}$$

The performance characteristics of individual classifier k can be specified by $P(u_k|H_j)$, where $P(u_k=1|H_0)=P_{fk}$=the probability of false alarm and $P(u_k=1|H_1)=P_{dk}$=probability of detection.

The global decision fusion classifier receives the decisions of the individual spatial classifiers as its inputs. The decision at the fused level, $$u = \varphi(u_1, u_2, \ldots, u_k) = \begin{cases} 0, & \text{global decision } H_0 \\ 1, & \text{global decision } H_1 \end{cases}$$

Depends only on spatial decision, there probability of detection $P_{dk}$, probability of false alarm $P_{fk}$ and how complementary they are to each other. Since multiple spatial LDA classifiers base their decisions on EEG raw signals in different temporal windows, the simplest assumption is that these decisions are statistically independent.

In an application such as RSVP in which stimuli 50 are presented at known time intervals to a human subject, a global window ("epoch") 52 of EEG data 54 sufficient to capture the entire temporal evolution of the brain response to the stimulus is extracted for each stimulus. Each global window is then classified separately. The global window is subdivided into multiple local windows 56 of EEG data so that each window captures a portion of the non-stationary response. The EEG data in the local windows are processed by the feature extractors and the features presented to the respective trained classifiers as described above.

Typically, an epoch of 900 ms was captured and subdivided into local windows spanning the entire epoch. Extensive testing has shown that a threshold window can be identified beyond which improvements to performance is negligible. The threshold window may be determined for specific human subjects and/or particular applications as the temporal evolution of the response will vary from subject-to-subject and may vary with the complexity of the brain response to a particular stimulus. Higher level cognitive responses generally taking longer to develop. Alternately, the threshold can be determined statistically for a group of subjects. A typical threshold window might be 450-500 ms. The use of a threshold window reduces the number of classifiers required to process the data and the latency to arrive at a decision.

In other types of applications stimuli occur randomly. The EEG data 60 is captured with a sliding window 62 and processed to capture the entire temporal evolution of the brain response for a task-relevant stimulus that occurs at an unknown time. The sliding window 62 has a duration of a local window e.g. 20-200 ms and more typically 50-100 ms, and suitably overlaps 25-50% as it slides in time. The EEG data captured by the sliding window 62 simultaneously represents the first time window for any stimulus that occurred within 0-50 ms, the second time window for any stimulus that occurred within 25-75 ms and so forth assuming a 50 ms window and 50% overlap. For purposes of example, we assume that a total window of 150 ms is required to capture the evolution of the brain response. This translates to five windows, hence five spatial classifiers.

The EEG data for sliding window 62 is simultaneously passed to the feature extractors 64 that extract the features for the five different windows. The extracted features are then suitably passed through respective delay elements 66 (1X=25 ms in this example) in order to time-align the data that is presented to the spatial classifiers 68. The classifiers process the features and generate their outputs 70. These time-aligned outputs are presented to temporal classifier 72 that generates a binary decision as to whether the sliding window (that occurred 100-150 ms ago) included a significant brain-response or not. The EEG data is continuously recorded, windowed and processed and the significant brain-response decision is generated (with a certain latency) in real-time to detect significant brain-responses. In this application, the identification of a threshold window again limits the number of classifiers and latency of the final decision.

It is important to note that the measured EEG data within a given window will include contributions from the various evolutionary time windows with respect to different stimuli occurring at different times. For example, a snapshot of the 'sliding window' might include window 1 data from a stimulus that just occurred, window 2 data from a stimulus that occurred 65 ms ago, window 4 data from a stimulus that occurred 100 ms ago and so forth. At best the different stimuli they reduce SNR and at worst they can trigger false positives to be detected e.g. a window 2 classifier outputs a significant brain-response true based not on window 2 data but based on a strong response evolving in window 4. Consequently, in order for this multi-window fused approach to be effective the individual classifiers must be robust e.g. each classifier must accurately detect significant brain-responses in its window and suppress significant brain responses from other windows. This means that the combination of extracted features and trained classifiers for the set of windows must be sufficiently different from each other. As it turns out, this is true for the non-stationary brain response triggered by task-relevant stimuli. The second level fusion to detect temporal patterns overcomes uncertainty or even errors in individual spatial classifiers to enhance classifier performance.

Figure 5A:
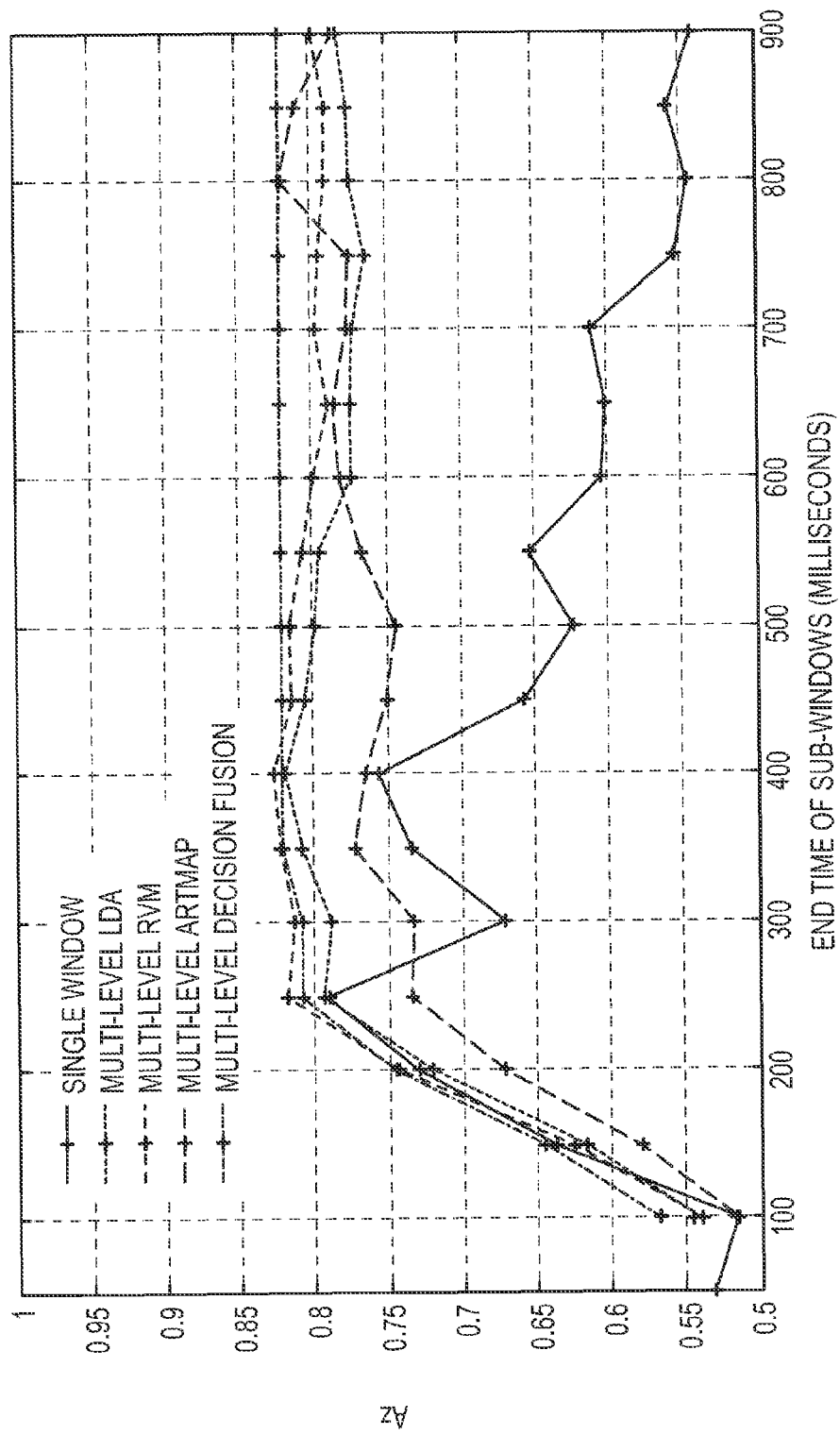
FIGS. 5a and 5b are plots of detection accuracy vs. time and of detection probability vs. false alarm rate comparing single and multi-window approaches, respectively.
Figure 5B:
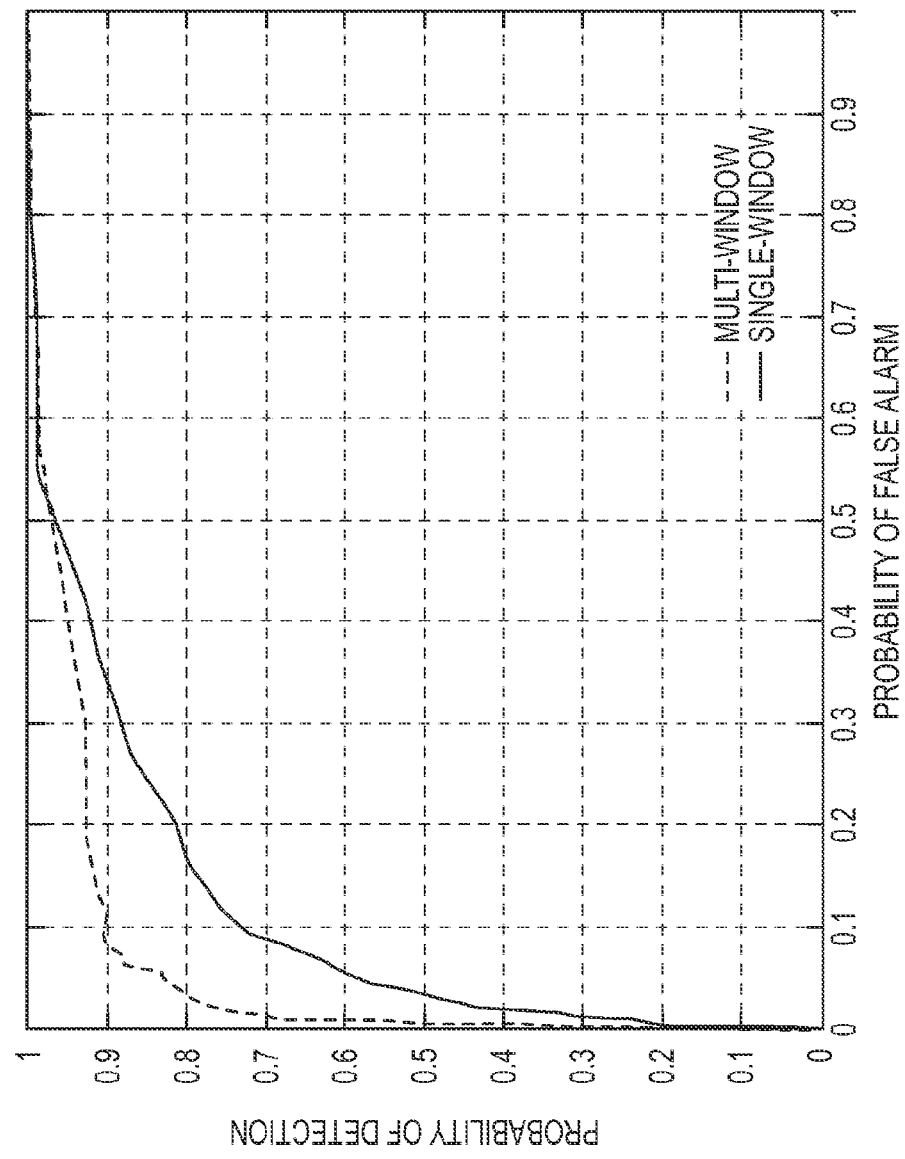

The effectiveness of the spatio-temporal classifier as compared to a single-window classifier is illustrated in FIGS. 5a and 5b. This experiment was conducted for an RSVP system using 50 ms non-overlapping windows. With a single sliding window, the area under ROC curve (Az) peaks at about 250 ms and again at 400 ms and falls off steadily. With a multi-window approach the Az increases with the addition of each new window to capture more of the evolving brain response and flattens out about 500 ms. The addition of more windows to capture and process data from 500 ms to 900 ms did not improve the results. The multi-window RVM and decision fusion configurations provided the best results.

The detection probability comparison is meaningless without a comparison of the false alarm probabilities, the two are inextricable. As shown in FIG. 5b, the multi-window approach (using decision-level fusion) substantially outperforms the single-window approach. For a given false alarm rate of 0.05, the detection probability increases from approximately 0.6 to 0.83. For a given detection probability of 0.85, the probability of a false alarm is reduced from 0.27 to 0.05. In detection applications, this represents substantial gains.

Fusion of Complementary Modalities

Although the spatio-temporal classifier and the described improvements thereto provide significant enhancements over the single-window spatial classifier, further improvements that continue to lower the false-alarm rate are needed for effective deployment of the technology. As will be described below, the fusion of complementary modalities such as time and frequency domain features and/or EEG and pupillary response enhance the detection of significant brain responses to task-relevant performance. The best performance is achieved by implementing these complementary modalities in the context of spatio-temporal classifiers although it is not necessary. Each modality generates an output indicative of the brain response and the decisions for the different modalities are then fused. Decision-level fusion is particularly effective for combining these modalities.

Fusion of Time-Domain and Frequency-Domain Classifiers

Reported EEG classifiers extract time-domain features e.g. signal amplitude, and classify the brain-response based on those features. As mentioned above, both time-domain features and frequency-domain features extracted from the raw EEG data can be presented to each of the spatial classifiers. The identification and extraction of a robust feature set are key to the performance of any classifier. Thus enriching the feature set presented to each spatial classifier should marginally improve the performance of the individual classifier to correctly detect significant brain-responses in the time window for which the classifier is trained and to reject insignificant brain-responses.

The fusion of time-domain and frequency-domain classifiers is an altogether different approach that enriches the detection of significant brain-responses. In this approach the time-domain and frequency-domain features are extracted from each window and directed to completely separate spatial or spatio-temporal classifiers that independently generate a decision level output for the brain state. An additional decision-level classifier is implemented to achieve an optimal combination of maximum likelihood estimates achievable between the two or more alternative and complementary decisions. For this approach to be effective the different time-domain and frequency-domain modalities must be complementary, not merely redundant. We discovered this to be true by observing different temporal patterns produced by the spatio-temporal classifier for the different features.

This can be understood by considering the competing models that attempt to explain the relationship between brain dynamics and cognitive dynamics. A popular and simple way to think about the relationship is to describe the sequence of brain areas that 'light up' during the various stages in the performance of a cognitive task. This evolving pattern across multiple channels is captured with the spatio-temporal classifier using multi-channel time signals such as voltage amplitudes. A more complex view treats the cognitive dynamics as reverberations of reentrant feedforward and feedback processes in a complex neural network or by the coordinated associated oscillations of neuron cell assemblies in a hebbian sense. The roles of oscillation synchronization (power enhancement) and oscillation de-synchronization (power block) and the associated oscillation pattern across multiple channels are captured with a spatio-temporal classifier using frequency signals such as power measurements in the delta, theta, alpha and/or bands. The science of cognitive dynamics focuses on either the 'light up' or 'oscillation' models. We have discovered that the information provided by the two different models is complementary and thus can be fused to improve detection performance.

Figure 6:
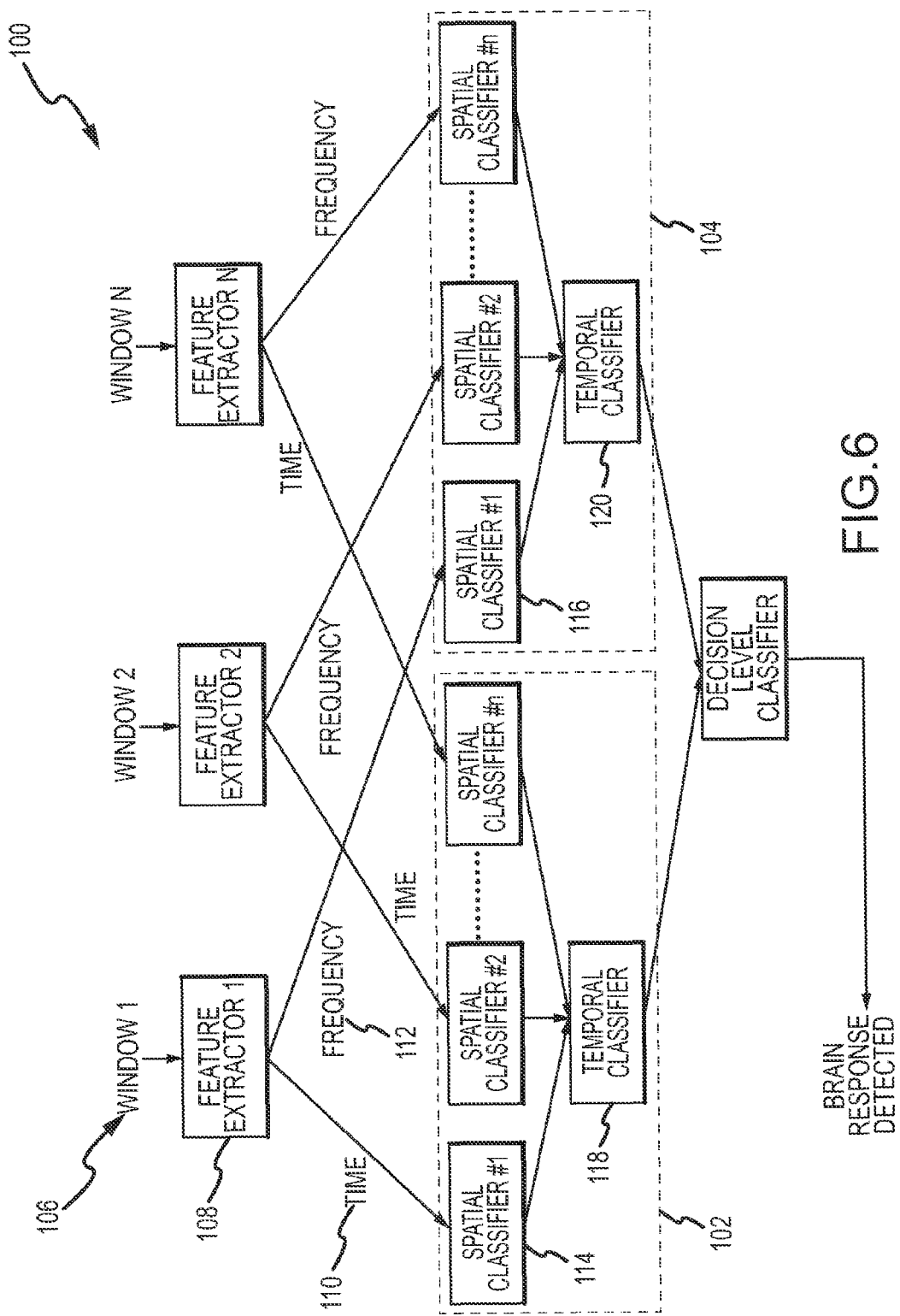
FIG. 6 is a diagram of a spatio-temporal classifier that performs the spatial and temporal classification based on time and frequency-domain features independently and fuses the results.

A classifier 100 that fuses the outputs of a spatio-temporal classifier 102 that classifies brain-response based on time-domain features and a spatio-temporal classifier 104 that classifies brain-responses based on frequency-domain features are illustrated in FIG. 6. Classifier 100 can be used in systems such as RSVP that control the presentation of stimuli or systems that use a sliding window to capture stimuli presented at unknown times. The EEG data is divided into windows 106 and provided to feature extractors 108 that extract the time and frequency-domain features for the particular window. In this example, the time-domain features 110 constitute the EEG voltage signals that are preprocessed to remove such artifacts as DC baseline drifts, abrupt changes caused by muscle movement and eye blink. The average voltage amplitude from 64 signal channels is subtracted from each channel signal. Other time-domain features can be derived from the raw EEG data. In this example, the frequency-domain features 112 constitute spectral power amplitude signals at different frequency bands, namely the delta band (1-4 Hz), theta band (4-8 Hz), alpha band (8-12 Hz), beta band (13-30 Hz) and gamma band (30-60 Hz). The different bands can be used individually or in combination. To extract the power signals, a continuous wavelet-transform (CWT) based time-frequency decomposition is performed on the multi-channel EEG. data. By choosing different types of wavelets and dilating/compressing them different time and frequency resolutions can be accessed in the time-frequency plane. The Discrete Wavelet Transform (DWT) and Short-Time Fourier Transform (STFT) are viable alternatives.

The time and frequency domain features 110, 112 are then presented to their respective spatio-temporal classifiers 102, 104. Each of these classifiers is similarly configured to the spatio-temporal classifier discussed previously in reference to FIG. 2. The only difference being that the individual spatial classifiers 114, 116 are trained on the time and frequency domain features, respectively. The temporal classifiers 118, 120 that fuse the level one outputs are preferably feature-level classifiers such as a LDA classifier that treat the individual spatial classifiers as features and generate a binary decision as to the state of the brain-response. The temporal-based classifier 118 captures the evolving activity levels of neurons at different spatial locations whereas frequency-based classifier 120 captures the underlying oscillation patterns associated with detection, decision making, attention and memory associative tasks.

Figure 7:
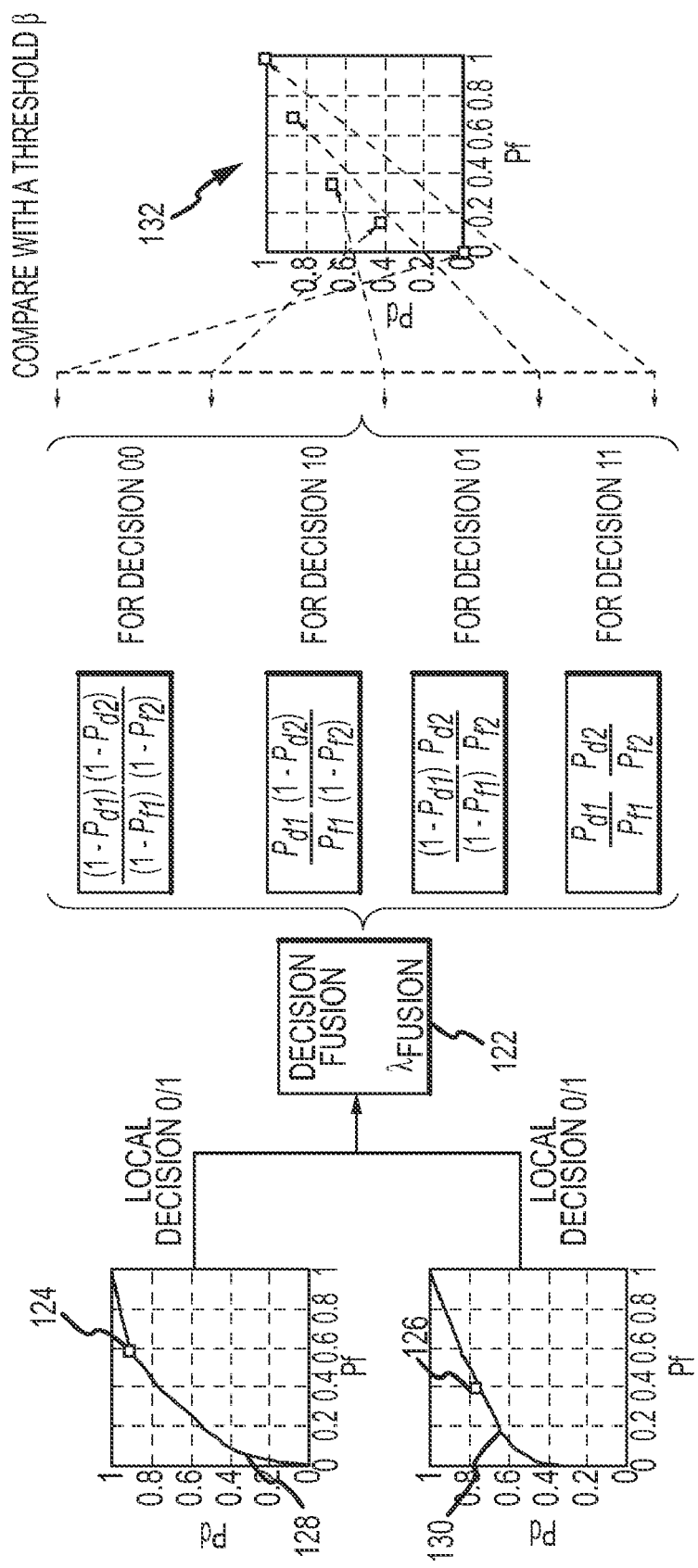
FIG. 7 is a block diagram of a decision-level fusion classifier fusing operating points on two separate ROC curves.

The decisions of the two complementary modalities are presented to a decision-level classifier 122. The Bayesian inference described previously and as illustrated in FIG. 7 is effective to combine the multiple hypotheses to improve overall classification performance. The decision level classifier 122 fuses two operating points 124, 126 from two separate ROC curves 128, 130 for the voltage and power-based classifiers. Five different fused operating points 132 can be generated depending on where the threshold is set against the fused likelihood ratio.

Figure 8A:
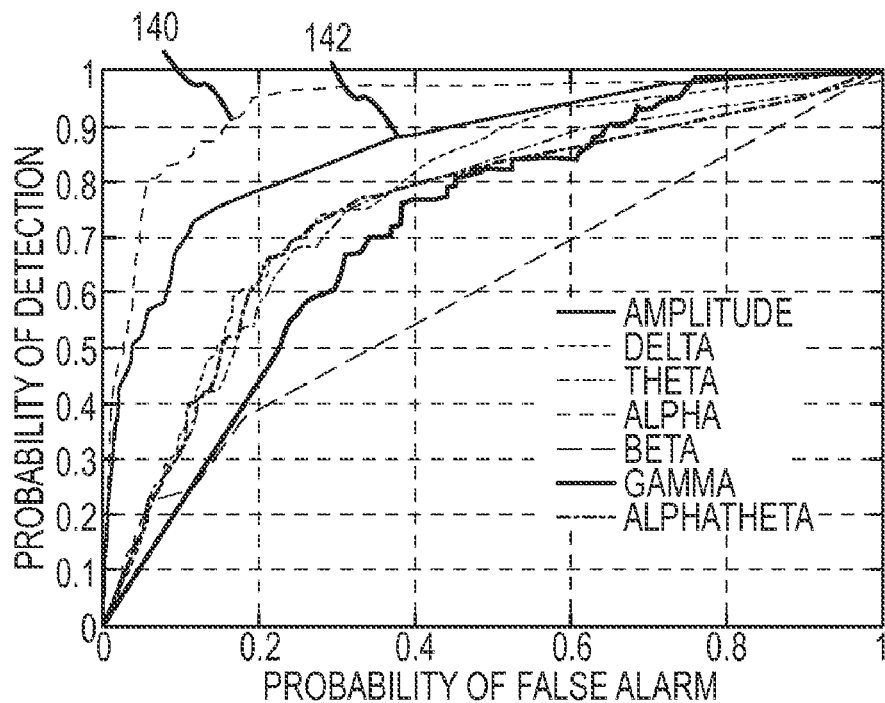
FIGS. 8a and 8b are ROC curves for a spatio-temporal classifier based on a single extracted feature and based on the independent combination of a time-domain and frequency-domain feature.
Figure 8B:
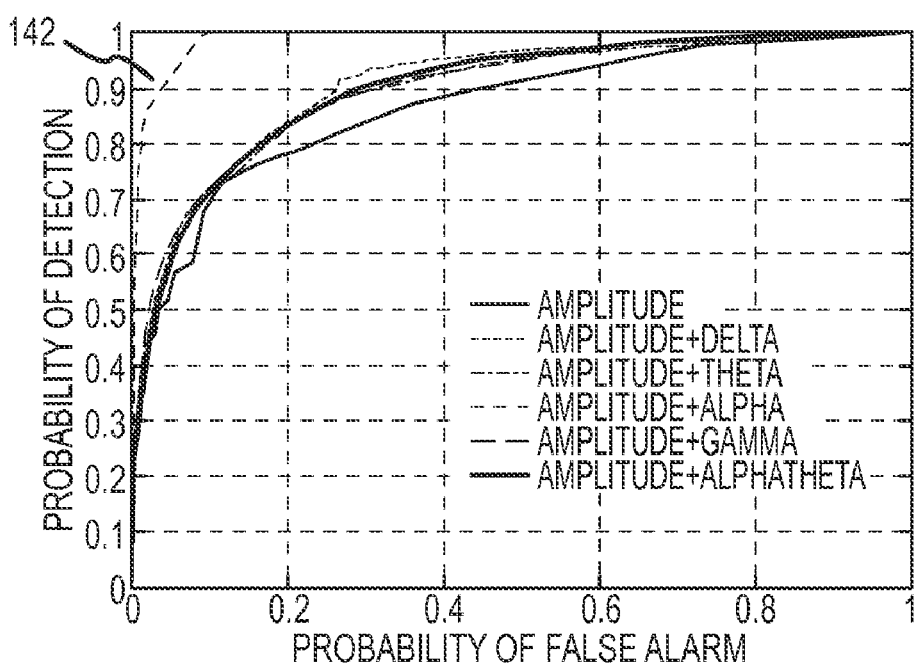

The performance gains achieved by fusing the results of the temporal and frequency classifiers are illustrated in FIGS. 8a-8b. The plots in FIGS. 8a and 8b represent the detection probability vs. false alarm probability for the separate and fused classifiers, respectively. The alpha-band power amplitude and voltage amplitude are the best performing separate classifiers as illustrated by plots 140, 142. Not surprising the combined amplitude+alpha classifier is the best fusion classifier as illustrated by plot 144. For a false alarm rate of 0.1, the fused detection probability is approximately 1.0 representing an improvement of about 0.18 over the alpha-band classifier and about 0.29 over the amplitude classifier. For a detection probability of 0.90, the fused false alarm rate is about 0.05 representing an improvement of about 0.13 over the alpha-band classifier and about 0.39 over the amplitude classifier. This is a demonstrable improvement of the spatio-temporal classifier. Given the enormous amount of data processed by typical systems the value of such a marked drop in the false alarm rate cannot be overstated.

Fusion of EEG and Pupillary Classifiers

The EEG-based classifiers, be they spatial or spatio-temporal, represent brain activities that are part of the central nervous system. The EEG signals provide fine time-resolution and spatial coverage over the scalp to detect the evolving cognitive processes going on at different areas of the brain. However, the EEG signals have to propagate through the scalp where they are distorted before measurement and interpretation by the EEG sensors and classification algorithms.

Pupil response provides a direct window that reveals sympathetic and parasympathetic pathways of the autonomic division of the peripheral nervous system. Task-evoked pupil dilations are known to be a function of the cognitive workload and attention required to perform the task. It has long been known that the pupil dilates in response to emotion evoking stimuli. Thus, cognitive task related pupillary response provides a modality that can be used to detect significant brain responses to single-trial task-relevant stimulus. Because the EEG and pupil responses are associated with different parts of the nervous system, specifically the brain area that triggers the pupillary response is deep inside the brain and thus not measurable by EEG electrons on the scalp, we hypothesized that the two could be complementary and that fusing the EEG and pupil classifiers would improve classification confidence. The fusion results confirmed our hypothesis.

Figure 9:
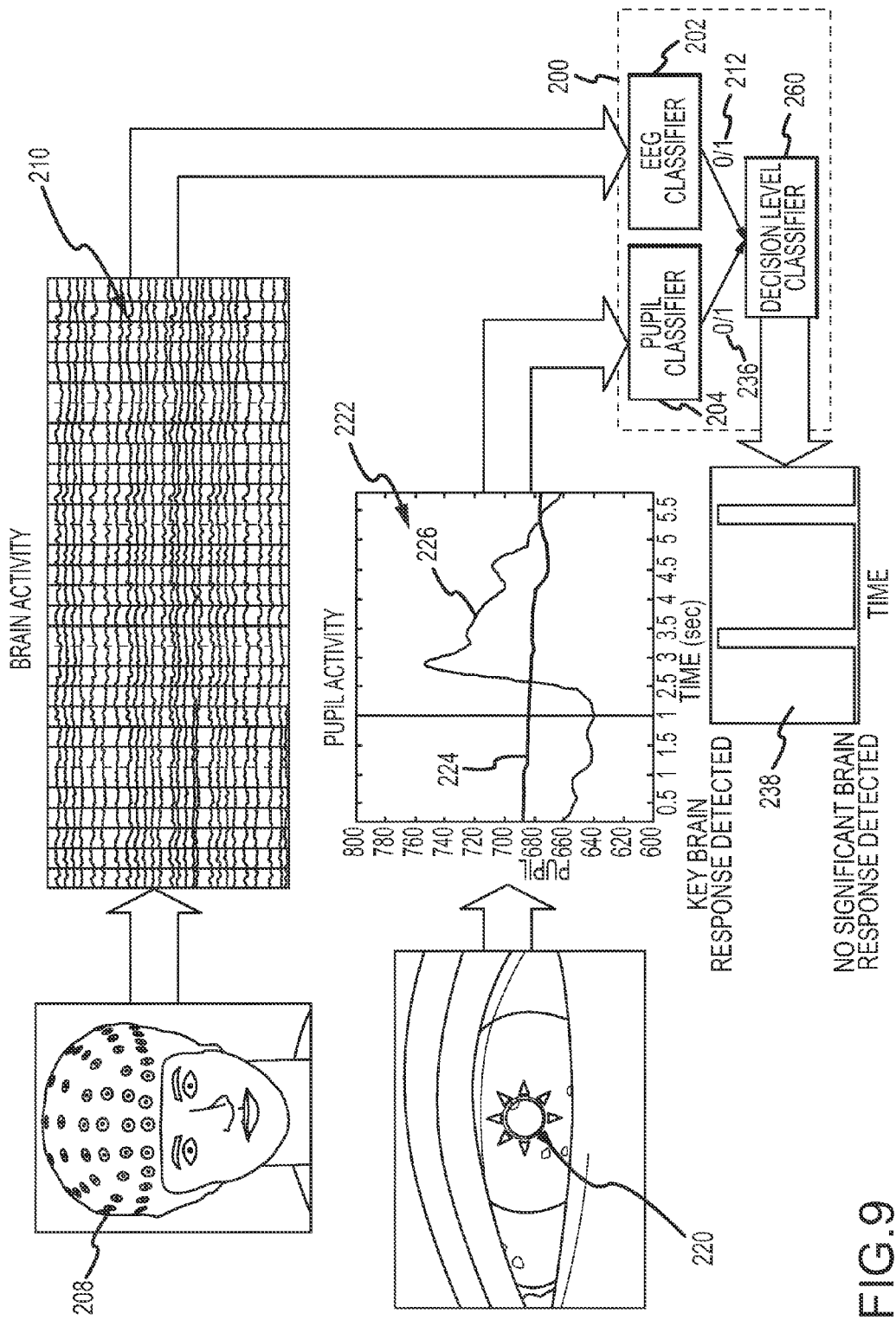
FIG. 9 is a diagram of a classifier that combines the results of an EEG classifier and a pupil classifier.
Figure 10:
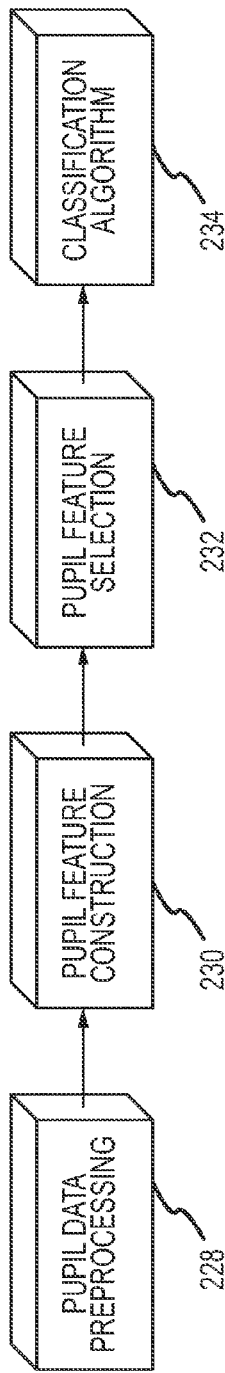
FIG. 10 is a flow diagram for the pupil classifier.

As illustrated in FIG. 9, a fused EEG-Pupillary classifier 200 includes an EEG classifier 202 and a pupil classifier 204 and a decision level classifier 206. EEG classifier 202 can be, for example a single window multi-channel classifier, a spatio-temporal classifier or a spatio-temporal classifier using fused time and frequency-domain classifiers. Electrodes 208 on the subject's scalp record EEG data 210 that is passed to EEG classifier 202 where it is subdivided into windows, features extracted, classification performed and possibly fused to generate a binary decision EEG output 212.

A camera such as an EyeLink 1000 video based eye tracking device is trained on the subject's pupil 220 to monitor pupil activity 222 e.g. size, continuously over time. The recording of pupil data is synchronized with EEG data acquisition. When presented with baseline stimulus or a distractor, pupil activity 224 is fairly flat. However, when presented with a task-relevant stimulus, pupil activity 226 indicates a fairly dramatic change. The pupil data is passed to pupil classifier 204 where it is pre-processed 228, pupil features constructed 230 and selected 232 and then classified 234 to generate a binary decision pupil output 236. The classification algorithm 234 can be selected from LDA, ARTMAP, RVM etc.

The continuous pupil size data is preprocessed 228 to remove all corrupted data associated with eye blinks or head movements. The data is interpolated to fill in the missing data. A moving average filter is then used to smooth the pupil area data to improve SNR. Pupil data is windowed into 1550 ms intervals commencing 300 ms before the onset of stimulus and ending 1250 ms after the stimulus onset. This can be done by capturing epochs in systems such as RSVP or using a sliding window when the stimulus timing is unknown.

As described previously, the decision-level classifier 206 is suitably based on a Bayesian inference. The decision level fusion optimal fuses the two decisions 212 and 236 based on the EEG and papillary modalities according to the operating points on their ROC curves at which of the decisions were made with certain probability of detection and probability of false alarm to generate a final decision 238 as to the brain-response state. Training data is used to obtain the ROC curves and choose the operating points associated with the EEG, papillary and decision-level classifiers.

Figure 11:
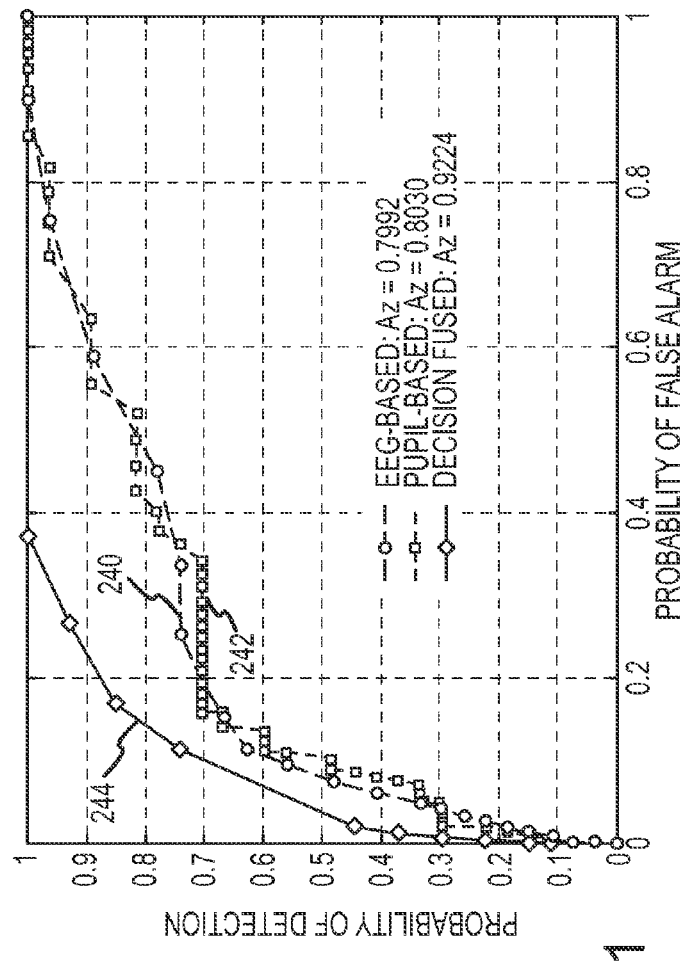
FIG. 11 is a ROC curve comparing the individual EEG and pupil classifier results to the fused results.

FIG. 11 plots detection probability versus false alarm probability for an EEG-based spatio-temporal classifier 240, a pupil-based classifier 242 and a fused EEG-Pupil classifier 242. For this specific example, the performance of the individual EEG and pupil classifiers is fairly similar. The fused classifier significantly outperforms either individual classifier.

RSVP System Using Multi--Modal Fusion

Figure 12:
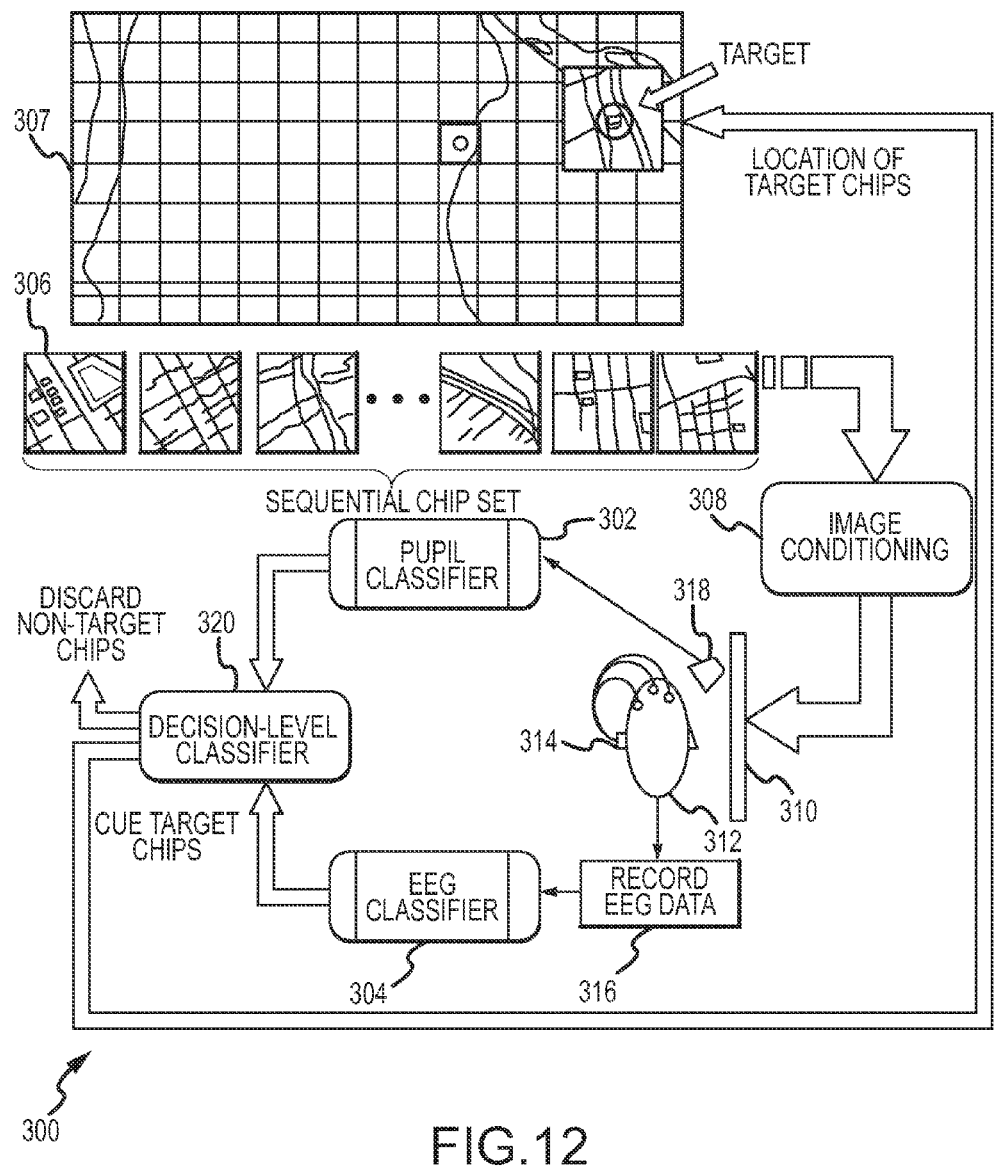
FIG. 12 is a diagram of an RSVP system using a fused spatio-temporal classifier in accordance with the present invention.

As illustrated in FIG. 12, an RSVP system 300 uses multi-modal fusion of a pupillary classifier 302 and an EEG classifier 304. The EEG classifier itself uses multi-modal fusion of voltage amplitude and power amplitude spatio-temporal classifiers, which in turn fuse the results of their respective spatial classifiers. In this example, image chips 305 from a large image or images 307 are conditioned 308 and displayed on display 310 at regular intervals to an analyst 312 having 64-channels of electrodes 314 attached to his or her scalp. The multi-channel EEG data is recorded 316 and passed to EEG classifier 304. A camera 318 records the pupil response and passes the pupil data to the pupil classifier 302. The decisions of the pupil and EEG classifiers are passed to a decision-level classifier 320 that decides whether the analyst's brain response to a particular image clip was 'significant' or not. If the decision is negative the image clips are discarded. If the decision is positive, the image clip is identified for closer examination.

The potential applications for an EEG-based classifier capable of single-event real-time detection of significant brain-responses triggered by task-relevant stimuli with acceptably low false alarm rates are numerous. The RSVP system for processing military or medical imagery is of great interest. The classifier could also be used to identify information that evokes a strong brain response from a person who is reading a book or surfing the web. The strong brain response could then be used to automatically gather additional information relevant to the passage or material that triggered the response. The classifier could be used as part of a warning system to detect, evaluate and neutralize threats to soldiers. The classifier could be used for lie detector technology.

While several illustrative embodiments of the invention have shown and described, numerous variations and alternate embodiments will occur to those skilled in the art. Such variations and alternate embodiments are contemplated, and can be made without departing from the spirit and scope of the invention as defined in the appended claims.

We claim:

1. A method of coupling human neural response with computer pattern analysis for enhanced single-event detection of significant non-stationary brain responses triggered upon occurrence of a task-relevant stimulus, comprising:
measuring EEG signals associated with a person's brain activity from a plurality of electrodes placed on the person's scalp;
subdividing the EEG signals into a plurality of different time windows;
extracting features from the EEG signals for each said different time window;
presenting the extracted features to a respective plurality of computer-implemented spatial classifiers trained to detect spatial patterns of said extracted features during different time windows from the occurrence of the task-relevant stimulus and to generate first level outputs indicative of the occurrence or absence of a significant brain response; and
presenting the spatial classifiers' first level outputs to a temporal classifier, said temporal classifier configured to implement feature-level fusion or decision-level fusion to detect temporal patterns across the different time windows relating to the evolution of the non-stationary brain response to task-relevant stimulus and to generate a second level output indicative of the occurrence or absence of the significant non-stationary brain response.

2. The method of claim 1,
wherein extracting features comprises extracting time-domain and frequency-domain features from the EEG signals in the different time windows,
wherein presenting the extracted features comprises presenting the time-domain features to a first plurality of computer-implemented spatial classifiers trained to detect spatial patterns of time-domain features and generate a first plurality of first level outputs and presenting the frequency-domain features to a second plurality of computer-implemented spatial classifiers trained to detect spatial patterns of frequency-domain features and generate a second plurality of first level outputs,
wherein presenting the first level outputs to a temporal classifier comprises presenting the first plurality of first level outputs to first temporal classifier to detect temporal patterns and generate a second level temporal output and presenting the second plurality of first level outputs to a second temporal classifier to detect temporal patterns and generate a second level frequency output,
further comprising presenting the second level temporal and frequency outputs to a decision-level classifier to generate a third level EEG output indicative of the occurrence or absence of the significant non-stationary brain response.

3. The method of claim 2, wherein the first and second temporal classifiers implement feature-level fusion.

4. The method of claim 2, wherein the frequency-domain features include a power metric in the alpha band.

5. The method of claim 1, further comprising:
measuring the person's pupillary response;
extracting pupil features from the pupillary response;
presenting the extracted pupil features to a computer-implemented classifier trained to detect patterns of extracted pupil features and to generate a pupil output indicative of the occurrence or absence of a significant brain response; and
combining the second level EEG output and the pupil output to generate a fused output indicative of the occurrence or absence of the significant brain response.

6. The method of claim 5, wherein the first level outputs are combined using feature-level fusion to generate the second level EEG output that is combined with the pupil output using decision-level fusion to generate the fused output.

7. The method of claim 1, wherein the temporal classifier comprises a feature-level fuser implemented using a probabilistic or recurrent learning method.

8. The method of claim 1, wherein the first level outputs are maximum likelihood estimates, said temporal classifier comprising a decision-level fuser that combines the first level outputs to achieve an optimal combination of the maximum likelihood estimates achievable.

9. The method of claim 1, wherein the EEG signals are subdivided into different overlapping windows of 20 ms to 200 ms in duration to capture the evolution of the non-stationary brain response.

10. The method of claim 1, wherein the EEG signals are subdivided into a plurality of different time windows up to a threshold time window beyond which classifier performance does not improve.

11. The method of claim 1, wherein the EEG signals are captured in a series of overlapping global windows each in sync with a known presentation of a stimulus and each global window is subdivided into a plurality of overlapping time windows up to a threshold time window, for each said global window the extracted features for a first said time window being presented to a first said spatial classifier and so forth to span the threshold time window and no further to generate said plurality of first level outputs.

12. The method of claim 1, wherein the EEG signals are captured by a sliding window, said features for each of the different time windows with respect to the occurrence of a task-relevant stimulus being extracted from the EEG signals captured by the sliding window and presented to the respective classifiers to generate the first level outputs with a known latency.

13. The method of claims 12, wherein either the features presented to the classifiers or the first level outputs generated by the classifiers are delayed according to the position of the time window with respect to the occurrence of the task-relevant stimulus to time-align the first level outputs for presentation to the temporal classifier.

14. The method of claim 12, wherein the sliding window is overlapped by approximately 25% to approximately 50% to capture the EEG signals, said sliding window having the same duration as each of the time windows.

15. A system for coupling human neural response with computer pattern analysis for enhanced single-event detection of significant non-stationary brain responses triggered upon occurrence of a task-relevant stimulus, comprising:
a plurality of electrodes for placement on a person's scalp;
a data collection system that measures EEG signals associated with the person's brain activity produced by the electrodes;

a data pre-processing system that windows the measured EEG signals into a plurality of different time windows;
a feature extractor that extracts both time-domain and frequency-domain features from the EEG signals in the respective time windows;
a first plurality of computer-implemented spatial classifiers trained to detect spatial patterns of the extracted time-domain features during different time windows from the occurrence of the task-relevant stimulus and to generate first outputs indicative of the occurrence or absence of a significant non-stationary brain response;
a first computer-implemented feature-level fuser trained to detect temporal patterns of the first outputs across the different time windows relating to the evolution of the non-stationary brain response and to generate a first decision indicative of the occurrence or absence of the significant non-stationary brain response;
a second plurality of computer-implemented spatial classifiers trained to detect spatial patterns of the extracted frequency-domain features during different time windows from the occurrence of the task-relevant stimulus and to generate second outputs indicative of the occurrence or absence of a significant non-stationary brain response;
a second computer-implemented feature-level fuser trained to detect temporal patterns of the second outputs across the different time windows relating to the evolution of the non-stationary brain response and to generate a second decision indicative of the occurrence or absence of the significant non-stationary brain response; and
a computer implemented decision-level fuser that provides an optimal combination of maximum likelihood estimates achievable between said first and second decisions to provide a fused decision for the occurrence of the significant non-stationary brain response.

16. A system for coupling human neural response with computer pattern analysis for enhanced single-event detection of significant non-stationary brain responses triggered upon occurrence of a task-relevant stimulus, comprising:
a plurality of electrodes for placement on a person's scalp;
a data collection system that measures EEG data signals associated with the person's brain activity produced by the electrodes;
a data pre-processing system that windows the measured EEG signals into a plurality of different time windows;
a first feature extractor that extracts EEG features from the EEG signals in the respective time windows;
a first plurality of computer-implemented spatial classifiers trained to detect spatial patterns of the extracted features during different time windows from the occurrence of the task-relevant stimulus and to generate first outputs indicative of the occurrence or absence of a significant non-stationary brain response;
a computer-implemented temporal classifier trained to detect temporal patterns of the first outputs across the different time windows relating to the evolution of the non-stationary brain response and to generate an EEG decision indicative of the occurrence or absence of the significant non-stationary brain response;
a camera system that measures the person's pupillary response;
a second feature extractor that extracts pupil features from the pupillary response;
a second computer-implemented classifier trained to detect patterns of extracted pupil features and to generate a pupil decision indicative of the occurrence or absence of a significant non-stationary brain response; and
a computer implemented decision-level fuser that provides an optimal combination of maximum likelihood estimates achievable between said EEG and pupil decisions to provide a fused decision for the occurrence of the significant non-stationary brain response.

17. A method of coupling human neural response with computer pattern analysis for enhanced single-event detection of significant non-stationary brain responses triggered upon occurrence of a task-relevant stimulus that occur randomly with unknown timing, comprising:
measuring EEG signals associated with a person's brain activity from a plurality of electrodes placed on the person's scalp;
using a sliding window that slides in time to segment the EEG signals into a sequence of time windows, the EEG signals captured by the sliding window simultaneously representing a plurality of different local windows positioned at different times with respect to an occurrence of a task-relevant stimulus;
for each said time window,
passing the EEG signals captured by the sliding window to a plurality of feature extractors that extract features from the EEG signals for the plurality of different local windows;
presenting the extracted features to a respective plurality of computer-implemented spatial classifiers trained to detect spatial patterns of said extracted features during the different local windows and to generate first level outputs indicative of the occurrence or absence of a significant brain response;
delaying either the features presented to the spatial classifiers or the first level outputs generated by the spatial classifiers according to the position of the corresponding local window to time-align the first level outputs; and
presenting the plurality of time-aligned first level outputs to a temporal classifier to detect temporal patterns across the different time windows relating to the evolution of the non-stationary brain response to task-relevant stimulus and to generate a second level output indicative of the occurrence or absence of the significant non-stationary brain response.

18. The method of claim 17, wherein the sliding window is overlapped by approximately 25% to approximately 50%.

19. The method of claim 17, wherein the sliding window has the same duration as each of the plurality of different local windows.

20. The method of claim 17, wherein the temporal classifier is configured to implement feature-level fusion or decision-level fusion.

* * * * *